US007681437B2

(12) United States Patent
Brinz et al.

(10) Patent No.: US 7,681,437 B2
(45) Date of Patent: Mar. 23, 2010

(54) DEVICE FOR DETERMINING THE VISCOSITY OF FLUIDS

(75) Inventors: Thomas Brinz, Bissingen A.D. Teck (DE); Jane Lewis, Wales (GB); Markus Tiefenbacher, Fellbach-Schmiden (DE); Thomas Geiger, Walddorfhaeslach (DE); Tobias Burk, Tuebingen (DE)

(73) Assignee: Robert Bosch GmbH, Stuttgart (DE)

(*) Notice: Subject to any disclaimer, the term of this patent is extended or adjusted under 35 U.S.C. 154(b) by 338 days.

(21) Appl. No.: 11/648,527

(22) Filed: Dec. 28, 2006

(65) Prior Publication Data

US 2007/0187196 A1 Aug. 16, 2007

(30) Foreign Application Priority Data

Dec. 28, 2005 (DE) ...................... 10 2005 062 718

(51) Int. Cl.
*G01N 11/06* (2006.01)
*G01N 11/14* (2006.01)

(52) U.S. Cl. ..................... 73/54.23; 73/54.14; 73/54.31

(58) Field of Classification Search ...... 73/54.11–54.38
See application file for complete search history.

(56) References Cited

U.S. PATENT DOCUMENTS 2,964,661 A * 12/1960 Sutherland et al. ............ 310/93
3,229,506 A * 1/1966 Bruss et al. ................ 73/54.28
3,889,140 A * 6/1975 Baermann ................... 310/103
4,062,225 A * 12/1977 Murphy et al. ............. 73/54.35
4,299,118 A * 11/1981 Gau et al. .................. 73/54.35
4,448,061 A * 5/1984 Brookfield ................. 73/54.33
4,463,291 A * 7/1984 Usry ..................... 318/400.26
4,817,416 A * 4/1989 Blanch et al. .............. 73/54.04
5,347,851 A * 9/1994 Grudzien et al. ........... 73/53.01
5,503,003 A * 4/1996 Brookfield ................. 73/54.32
5,746,294 A * 5/1998 Lee ............................ 188/163
5,900,539 A * 5/1999 Tremblay et al. .......... 73/54.13
6,182,503 B1 * 2/2001 Mode et al. ................ 73/54.04
6,951,127 B1 * 10/2005 Bi ............................ 73/54.37
7,051,846 B2 * 5/2006 Lee ............................ 188/161
2001/0037673 A1 * 11/2001 Jackson ..................... 73/54.23
2002/0139175 A1 * 10/2002 Price ......................... 73/54.16
2006/0070428 A1 * 4/2006 Bateson et al. ............. 73/54.32
2006/0075805 A1 * 4/2006 Moonay .................... 73/54.28

FOREIGN PATENT DOCUMENTS

DE 24 44 148 3/1976

* cited by examiner

*Primary Examiner*—Christopher P Schwartz
(74) *Attorney, Agent, or Firm*—Kenyon & Kenyon LLP

(57) ABSTRACT

A device for determining the viscosity of fluids. The device includes an injector, which has a piston and a hollow cylinder with a nozzle. The device further includes a cannula. The device also includes a forward-feed device with the aid of which the piston is displaceable at a uniform speed.

8 Claims, 2 Drawing Sheets

DEVICE FOR DETERMINING THE VISCOSITY OF FLUIDS

FIELD OF THE INVENTION

The present invention relates to a device for determining the viscosity of fluids.

BACKGROUND INFORMATION

A device for determining the viscosity of fluids is described in German Patent No. DE 24 44 148 A1. In addition to an injector, which has a piston and a hollow cylinder including a nozzle, this device has a cannula and a forward-feed device by which the piston is displaceable at a uniform speed. To calculate the viscosity of a fluid, a pressure sensor measures the pressure of the fluid to be measured directly in front of the cannula through which the fluid to be measured is pressed. This makes direct contact between the pressure sensor and the fluid to be measured unavoidable and also the then required cleaning of the pressure sensor after each measurement.

SUMMARY

An object of the present invention is to provide a device for determining the viscosity of fluids in which the viscosity is determined without direct contact of a measuring device with the fluid to be measured.

In accordance with an example embodiment, a device for determining the viscosity of liquids is distinguished by the possibility of measuring the force exerted on the piston by the forward-feed device, using a force-measuring device.

Through the use of a force-measuring device between the piston and the forward-feed device, it is possible to ascertain, without direct contact of the measuring device with the liquid to be measured, a characteristic quantity in the form of a force that, together with other characteristic quantities and under the precondition of a piston moving at a defined speed and/or a known volume flow, allows a calculation of the viscosity of the liquid to be measured. This dispenses with the cleaning of a measuring device which is in direct contact with the fluid. It saves considerable time in connection with the process time to be scheduled for a measurement and it simplifies the configuration of semi-automatic and fully automatic devices. This contact-free measurement has an additional advantage when determining the viscosity of aggressive fluids since, in contrast to the conventional device, no additional measures for protecting the measuring device from the aggressive fluid will have to be taken.

According to an advantageous specific embodiment of the present invention, the cannula is placed directly on the nozzle of the hollow cylinder of the injector, avoiding an intermediate piece. In this way only disposable parts, i.e., piston, hollow cylinder and cannula, come into contact with the fluid to be measured. The device may thus immediately be used for another viscosity determination without having to undergo any cleaning whatsoever.

According to an embodiment of the present invention, the feed-forward device and the piston are connected by a clutch. This allows a rapid and uncomplicated exchange of the injector.

Furthermore, the example device is equipped with an electronic memory configured to store the force determined by the force-measuring device, or the force characteristic determined by the force-measuring device. As a result, the device may be operated at least partially independently of a person monitoring the measurements, and thus in a cost-effective manner.

In addition, the example device is equipped with an electronic processing unit, an input unit, and a display unit. This allows wide-scale automation of the viscosity determinations and the integration of the device into a network.

Moreover, when equipping the device with at least one manipulator by which the injector and/or the cannula are/is able to be inserted in and/or removed from a holder that is part of the device, it is possible to design a fully automatic device for determining the viscosity of fluids since only the injector and the cannula must be changed between individual measurements.

The present invention also provides an integration of the device into a system. This makes it possible to operate the device in a production and/or measuring line.

Moreover, it is provided to use the device as metering device. With the aid of such a metering device, the viscosity of the fluid to be metered may be recorded simultaneously with the metering process. This leads to considerable time savings and reduces the investment in machinery and measuring technology.

BRIEF DESCRIPTION OF THE DRAWINGS

Additional details of the present invention are described with the aid of a schematically represented exemplary embodiment and a diagram.

DETAILED DESCRIPTION OF EXAMPLE EMBODIMENTS

Figure 1:
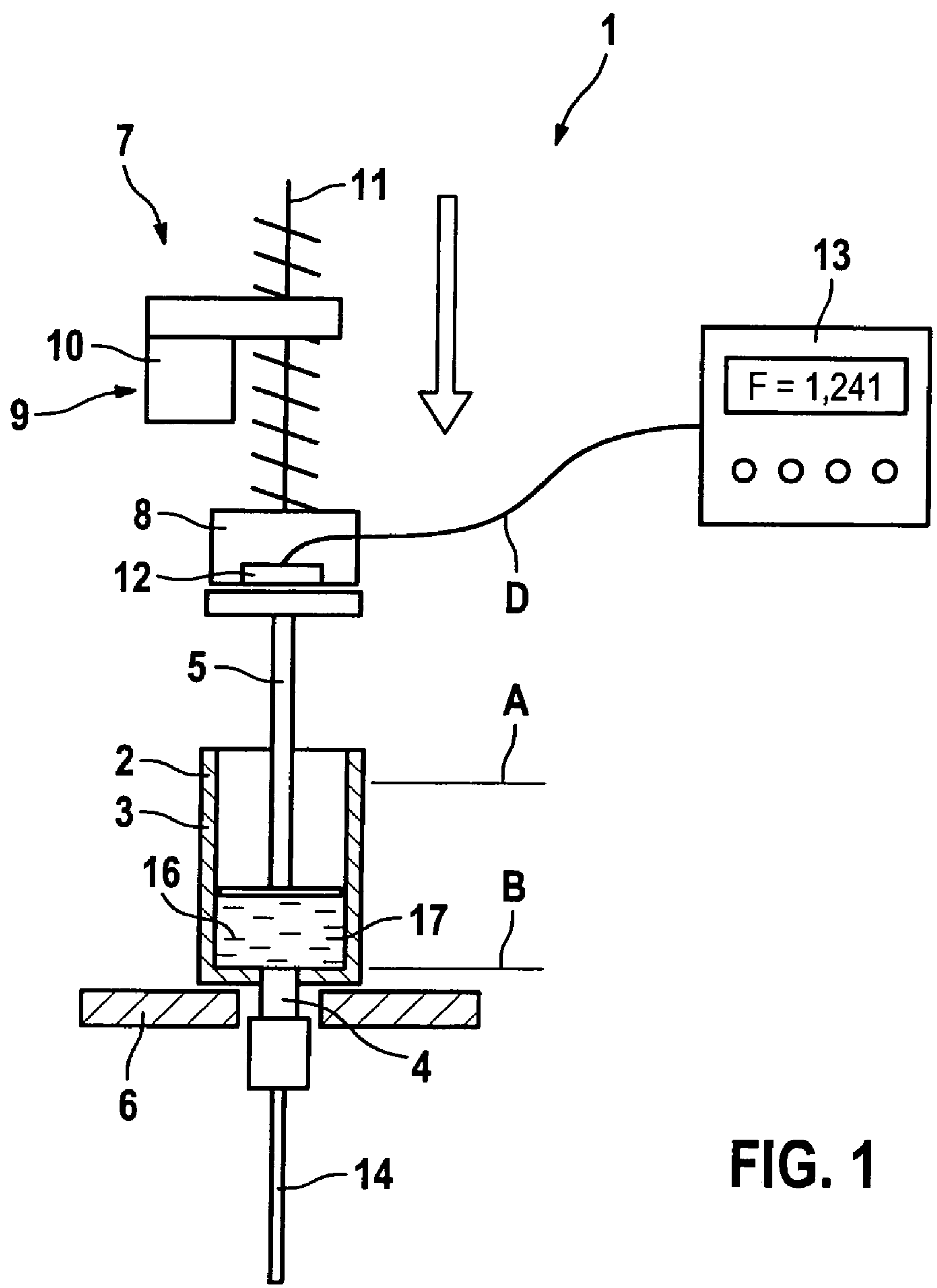
FIG. 1 shows a schematic view of a device according to an example embodiment of the present invention.

FIG. 1 shows a device 1. Device 1 includes an injector 2, which has a hollow cylinder 3 including a nozzle 4, a piston 5 being guided inside hollow cylinder 3. Injector 2 is supported in a schematically shown holder 6 so as to be releasable. In addition, device 1 includes a forward-feed device 7. Forward-feed device 7 is made up of a clutch 8 (schematically illustrated) by which piston 5 is able to be displaced, and a drive 9. Drive 9 is configured to displace piston 5 at a constant speed in a direction of arrow x, via clutch 8. Schematically shown drive 9 includes an electromotor 10 and a spindle 11 for this purpose. A sensor 12 of a force-measuring device 13 is situated in clutch 8, a pressure force, or expression force F, at which drive 9 together with spindle 11 is acting on piston 5 via clutch 8 being recordable with the aid of force-measuring device 13. Sensor 12 transmits the recorded data via a data line D. Finally, device 1 also includes a cannula 14 and a catch basin 15. The cannula or disposable capillary 14 is placed atop nozzle 4 of hollow cylinder 3 of injector 2. During the displacement of piston 5 with the aid of drive 9, from an original position A to a final position B, a fluid or fluid sample 16 to be measured is pressed from an interior 17 of hollow cylinder 3 through nozzle 4 and cannula 14, into catch basin 15 at a constant fluid flow. Interior 17 of injector 2 preferably has a maximum volume of 2 ml to 100 ml. The dimensions of nozzle 3 and cannula 14 are adapted to the fluid to be measured and to the volume flow at which the fluid is expressed.

Injector 2 and cannula 14 are preferably designed as disposable components of device 1. That is to say, a new injector and a new cannula are used for each viscosity determination.

According to a variant of an embodiment (not illustrated) of the device, the device also includes at least one manipulator by which the injector and/or the cannula are/is able to be exchanged. A separate holder may naturally be provided for the cannula.

According to a variant of an embodiment of FIG. 1, the force-measuring device is placed between the holder and the hollow cylinder. Given such a set-up, stressing of the data line of the measuring device by a movement of the piston is avoided.

Figure 2:
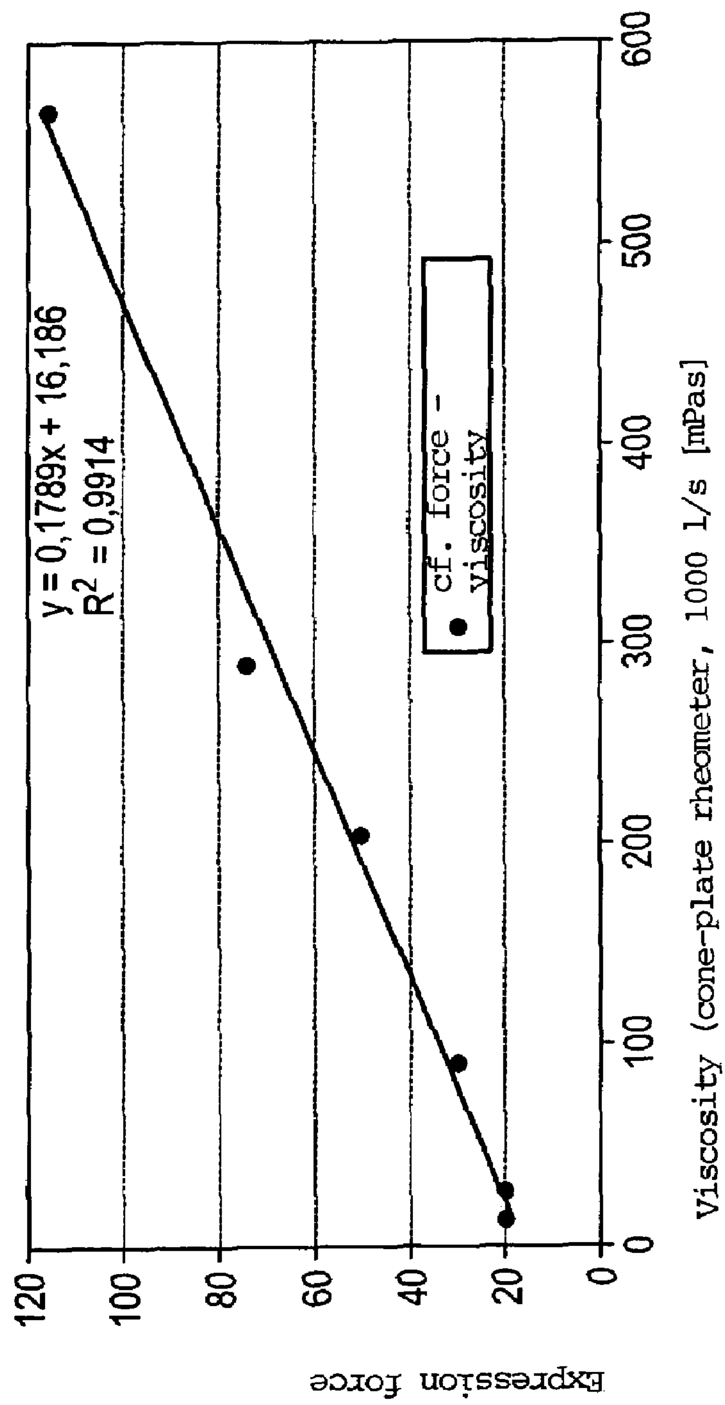
FIG. 2 shows a diagram.

FIG. 2 shows a diagram from which the viscosity of an examined fluid is able to be read out as a function of a measured expression force F. The calculations are generally based on the following data:

length of the cannula: 1.5"

diameter of the cannula: 1.33 mm volume flow when injector is squeezed out: 120 ml/min The Hagen-Poiseuille law as well as the cannula data (length and inner diameter), the measured force and the piston forward-feed speed are utilized to calculate the viscosity. The pressure differential is the difference between the internal peak pressure, which may be calculated from the measured force, and the ambient pressure. To increase the accuracy of the viscosity determination of fluids with the aid of the expression force, the present invention provides correction of the measured force or the measured force characteristic by the amount of friction of the piston inside the hollow cylinder of the injector.

In the present example, the measurement of the expression force is indicated in Newton, and the viscosity in mPas.

The present invention is not restricted to the illustrated or described exemplary embodiments. Instead, it includes further embodiments. For example, the present invention provides an integration of the device into equipment for metering and application processes in which fluids are already expressed at a constant volume flow. This minimizes the technical effort for determining the viscosity.

What is claimed is:

1. A device for determining viscosity of a fluid, comprising:

an injector including a piston and a hollow cylinder having a nozzle, the injector being supported in a holder;

a cannula;

a forward-feed device adapted to displace the piston at a uniform speed; and a force measuring device adapted to measure a force exerted on the piston by the forward-feed device;

wherein the force-measuring device is situated between the holder and the hollow cylinder.

2. The device as recited in claim 1, wherein the cannula is directly on the nozzle of the hollow cylinder of the injector without an intermediate piece.

3. The device as recited in claim 1, wherein the forward-feed device and the piston are connected by a clutch.

4. The device as recited in claim 1, further comprising:

an electronic memory in which one of: the force determined with the aid of the force-measuring device is stored, or a force characteristic determined with the aid of the force-measuring device is stored.

5. The device as recited in claim 1, further comprising:

an electronic processing unit;

an input device; and a display unit.

6. The device as recited in claim 1, further comprising:

at least one manipulator by which at least one of the injector and the cannula is able to be at least one of inserted in and removed from a holder, which is part of the device.

7. The device as recited in claim 1, wherein the device is integrated into a system.

8. The device as recited in claim 1, wherein the device is a metering device.

* * * * *